(12) United States Patent
Lu et al.

(10) Patent No.: US 6,188,927 B1
(45) Date of Patent: Feb. 13, 2001

(54) IMPLANTABLE CARDIAC STIMULATION SYSTEM HAVING IMPROVED METHOD OF CALIBRATING PHYSIOLOGIC SENSORS

(75) Inventors: Richard Lu, Thousand Oaks; David W. Adinolfi, Valencia, both of CA (US)

(73) Assignee: Pacesetter, Inc., Sylmar, CA (US)

(*) Notice: Under 35 U.S.C. 154(b), the term of this patent shall be extended for 0 days.

(21) Appl. No.: 09/292,905

(22) Filed: Apr. 16, 1999

(51) Int. Cl.[7] .................................................. A61N 1/365
(52) U.S. Cl. .............................................. 607/17; 607/28
(58) Field of Search .......................................... 607/17–28

(56) References Cited

U.S. PATENT DOCUMENTS

| | | | |
|---|---|---|---|
| 4,399,820 | 8/1983 | Wirtzfeld et al. | 128/419 |
| 4,644,954 | 2/1987 | Wittkampf et al. | 128/419 |
| 4,759,366 | 7/1988 | Callaghan | 128/419 |
| 4,865,036 | 9/1989 | Chirife | 128/419 |
| 4,867,163 * | 9/1989 | Shaldach | 607/9 |
| 5,076,271 * | 12/1991 | Lekholm et al. | 607/9 |
| 5,154,171 | 10/1992 | Chirife | 128/419 |
| 5,303,702 * | 4/1994 | Bonnet et al. | 607/20 |
| 5,476,487 * | 12/1995 | Sholder | 607/28 |
| 5,562,712 | 10/1996 | Steinhaus et al. | 607/20 |
| 5,626,622 | 5/1997 | Cooper | 607/18 |
| 5,707,398 | 1/1998 | Lu | 607/27 |
| 5,755,740 * | 5/1998 | Nappholz | 607/18 |
| 5,941,904 * | 8/1999 | Johnston et al. | 607/19 |
| 6,044,297 * | 3/2000 | Sheldon et al. | 607/17 |

* cited by examiner

Primary Examiner—Jeffrey R. Jastrzab

(57) ABSTRACT

An implantable cardiac stimulation system is disclosed which automatically optimizes its ability to rate-responsively pace by enabling calibration when the patient is at rest and has a functioning lead. Devices which employ physiologic sensors are based on a baseline value of the sensor signal corresponding to the resting state. Accordingly, the control system determines if the patient is at rest using a suitable sensor and also determines if the lead impedance is within normal values, i.e. functional and intact. If these conditions are met, the control system stores the current baseline of the sensor at rest and proceeds with normal sensing and stimulation commands until the next calibration is performed. In addition, the system can automatically calibrate a sleep value for the physiologic sensor using a sensor which can detect the sleep state. While the preferred embodiment discloses a minute ventilation sensor, other closed-loop sensors are contemplated, including at least paced depolarization integral (PDI), QT interval and pre-ejection interval (PEP).

16 Claims, 3 Drawing Sheets

IMPLANTABLE CARDIAC STIMULATION SYSTEM HAVING IMPROVED METHOD OF CALIBRATING PHYSIOLOGIC SENSORS

FIELD OF INVENTION

This invention relates to an implantable cardiac stimulation device which monitors a physiologic parameter of a patient's heart to determine stimulation rates, and more particularly to an implantable dual sensor rate-responsive stimulation device that reliably calibrates the rate-responsive sensor and permits automatic calibration post-implant.

BACKGROUND

Implantable cardiac stimulation devices include devices such as cardiac pacemakers, cardioverters, and/or defibrillators. These devices stimulate the heart to maintain a patient's cardiac activity to meet metabolic needs. Originally, pacemakers stimulated the heart at a fixed rate. This did not provide an adequate heart rate based upon changes in the physiologic and metabolic needs of the patient.

It has been recognized that it is necessary to monitor physiologic and metabolic parameters to change the stimulation rate as indicated by the activity and stress levels of the patient. It has also been recognized that there is a need to monitor multiple sensors to determine the indicated stimulation rate.

These sensors can include minute ventilation (also known as minute volume), paced depolarization integral (PDI) (also known as ventricular gradient), QT interval, activity level, activity variance, temperature, oxygen saturation, the inclination of the patient's body, pre-ejection period (PEP), etc.

This invention is drawn towards the sensors which require a baseline measurement, typically at rest, and preferably not during sleep. Such sensors include minute ventilation (also known as minute volume), paced depolarization integral (PDI), QT interval, and pre-ejection period (PEP), oxygen saturation, temperature, among others. Such sensors tend to rely on the integrity of the stimulation lead for proper operation. A few of these sensors also have a tendency to drift out of calibration due to the patient's changing exercise needs, medications, etc.

As a result, a method of calibration is useful for any sensor which is dependent upon lead integrity for proper operation and/or which requires periodic re-calibration. It is also desirable to determine a sleep value, below the alert resting state, to enable patients to achieve a lower pacing rate while sleeping.

The minute ventilation of a patient, for example, is based on tidal volume and respiration rate, which may be detected by measuring the amplitude and rate of a patient's respiration impedance signal. The measurement of minute ventilation is well known (see, for example, U.S. Pat. No. 5,562,712, issued Oct. 8, 1996 to Steinhaus et al., entitled "Minute Volume Rate-Responsive Pacemaker using Dual Unipolar Leads"). Briefly, the impedance signal may be obtained through the use of a controller applying a measuring current between a first electrode and a reference point on the pacemaker, typically the housing, sometimes referred to as the case electrode. The impedance can then be measured, typically, between a second electrode and the reference point. This impedance measurement of the patient varies as a function of the patient's pleural pressure, and therefor the impedance represents the patient's minute ventilation.

U.S. Pat. No. 5,707,398, issued Jan. 13, 1998 to Lu, entitled "Automatic Determination of Optimum Electrode Configuration for a Cardiac Pacemaker" sets forth a stimulation system which recognizes the need to monitor the lead impedance for changes. This system monitors the response of each electrode and then chooses the optimal electrode to monitor and measure the minute ventilation. However, this system does not address the need to test the lead impedance as a condition prior to calibrating the baseline value. Rather, it automatically selects the pair which provides optimal performance.

To calibrate the baseline value of a device employing minute ventilation, the controller must be operating under known conditions, that is, the patient must be at rest and not sleeping. Many sensors can be used to indicate when the patient is at rest and/or in a sleep state; such sensor signals include the activity level, the activity variance, and possibly the inclination of the patient. See, for example, U.S. Pat. No. 5,626,622, issued May 6, 1997 to Cooper, entitled "Dual Sensor Rate-Responsive Pacemaker", which shows the use of an activity sensor to determine the activity level of the patient. See, for example, U.S. Pat. No. 5,476,483, to Bornzin et al., entitled "System and Method for Modulating the Base Rate During Sleep for a Rate-responsive Cardiac Pacemaker", which shows the use of activity variance to determine if the patient is at rest or sleeping.

Accordingly, it is desirable to develop an implantable cardiac stimulation device which can perform an enhanced calibration of its baseline level upon implantation (i.e., by performing a self-test of the lead system and verifying that the patient is at a suitable resting state) and to automatically and periodically recalibrate the baseline at appropriate intervals to ensure the correct stimulation rate may be determined for the patient.

SUMMARY OF THE INVENTION

The present invention is directed toward an implantable rate-responsive stimulation device that reliably calibrates the rate-responsive sensor at rest, both at implant and automatically post-implant.

To this end, the present invention is directed toward any physiological sensor that must have a baseline value that needs to be calibrated at rest and uses a properly functioning implantable lead to detect a physiological parameter of the heart. While the preferred embodiment is directed toward a minute ventilation sensor, other sensors may include the paced depolarization integral (PDI), QT interval, pre-ejection period (PEP), oxygen saturation, etc.

To insure the optimal stimulation rate, the cardiac pacemaker must know the baseline value of the physiological sensor corresponding to a resting state. Accordingly, the baseline value is typically measured at implant when the patient is observed to be resting.

As set forth above, physiological sensors must be periodically re-calibrated due to patient changes and lead changes such as medication changes, lifestyle changes, lead aging, lead dislodgment, etc.

To reliably calibrate the baseline value at rest, the controller of the present invention determines if the patient is at rest using a second sensor, such as an activity sensor or any additional sensor which is not being calibrated. Since the rate-responsive sensor is of the type that relies on a functioning lead, the controller also determines if the lead impedance is within normal limits indicating a properly functioning lead system. If the lead impedance is within normal limits and the patient is at rest, the controller measures a current sensor value and stores such measurement as the baseline.

The present invention further contemplates measuring a sensor value during the sleep state to permit a lower pacing rate during sleep.

Accordingly, in another embodiment, calibration may be performed with sleep as the baseline value, adjusting, mapping or taking a second calibration to determine an appropriate value for the resting state.

Finally, the present invention contemplates a method of reliably calibrating the baseline value by confirming that the patient is at rest (e.g., "alert-resting" or sleeping) and performs a lead impedance test to prevent an automatic calibration with a defective lead.

DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE PREFERRED EMBODIMENTS

Figure 1:
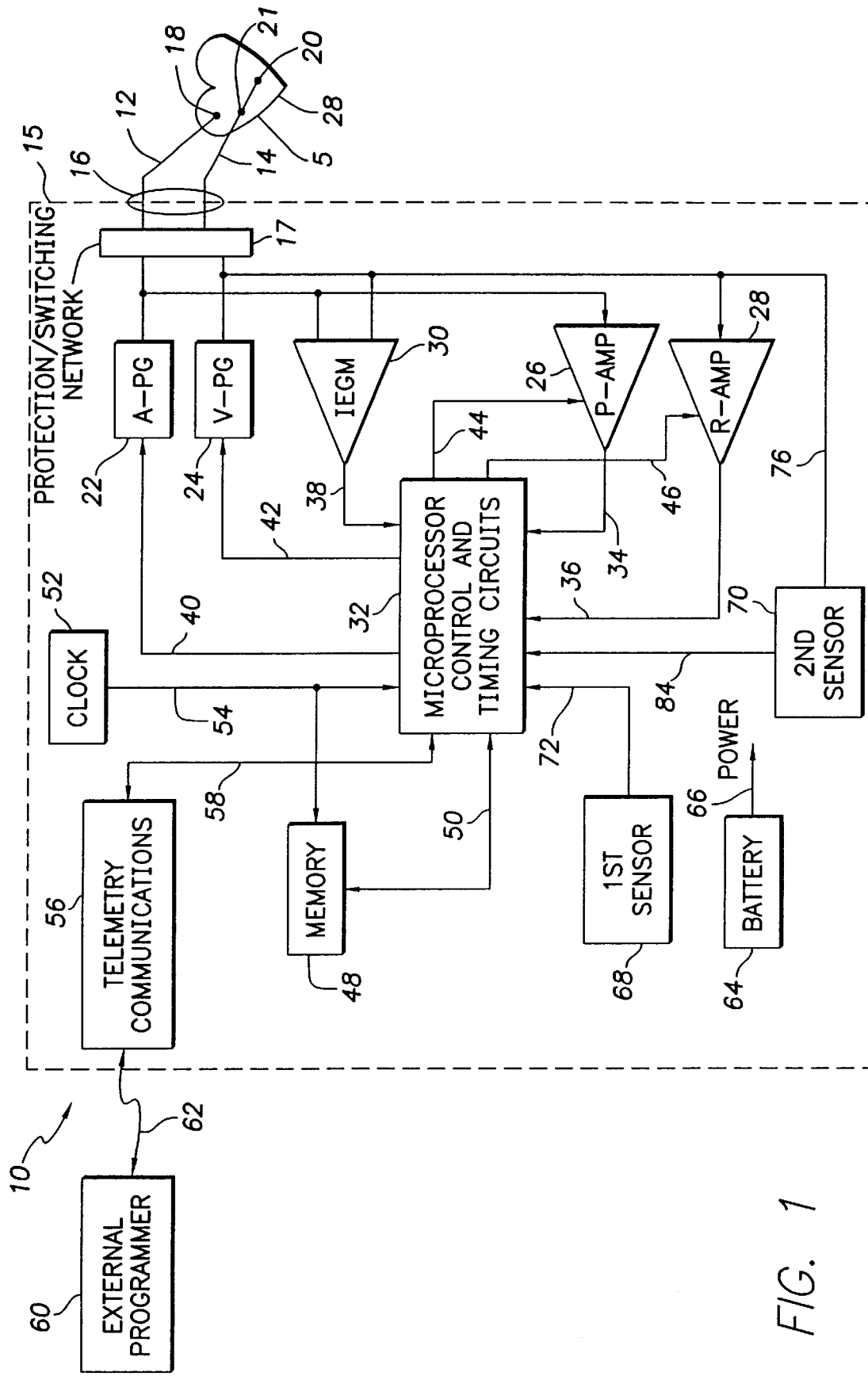
FIG. 1 shows a simplified functional block diagram of an implantable stimulation device according to the present invention.

In FIG. 1, the implantable cardiac stimulation device in accordance with the present invention is illustrated as a dual sensor rate-responsive pacemaker 10.

While the preferred embodiment is directed towards a system which employs a minute ventilation sensor and an activity sensor, it is well within the scope of the invention to include the present calibration system in any implantable cardiac pacemaker that employs a physiologic sensor which must be calibrated at rest, such as paced depolarization integral (PDI), QT interval, pre-ejection period (PEP), oxygen saturation, etc., and to use any additional sensor that indicates when the patient is at rest and that does not require calibration. The present invention further contemplates a system that can measure the physiologic sensor during a sleep state, and determine an appropriate pacing rate during sleep.

FIG. 1 sets forth a simplified block diagram of the implantable pacemaker 10. The pacemaker 10 is coupled to a heart 5 by way of two leads 12, 14, the atrial lead 12 has at least one electrode 18 in contact with an atria of the heart 5. The ventricular lead 14 has, preferably, a ring electrode 21 proximal to a tip electrode 20 which is in contact a ventricle of the heart 5. The leads 12, 14 are electrically and physically connected to the pacemaker 10 through a connector 16 that forms an integral part of the housing 15 where the circuits of the pacemaker are housed.

The connector 16 is electrically connected to a protection/switching network 17, which network 17 switchably couples the electrodes to the appropriate sensing and pacing configuration and to the appropriate measurement circuitry (such as a lead impedance circuitry, minute ventilation impedance circuitry, or other physiologic measuring circuitry, such as physiologic sensor 70). The network 17 further electrically protects circuits within the pacemaker 10 from excessive shocks or voltages that could appear on the electrodes 18, 20 in the event such electrodes 18, 20 were to come in contact with a high voltage signal, e.g., from a defibrillator shock.

The leads 12, 14 carry the stimulating pulses to the heart 5 from an atrial pulse generator 22 and a ventricular pulse generator 24, respectively. Further, electrical signals from the atria are carried from the electrode 18, through the lead 12 to the input terminal of an atrial channel sense amplifier 26, and electrical signals from the ventricles are carried from the electrodes 20, 21 through the lead 14 to the input terminal of a ventricular channel sense amplifier 28.

Similarly, electrical signals from both the atria and ventricles are applied to the inputs of the IEGM (intracardiac electrogram) amplifier 30. The amplifier 30 is a broad band amplifier typically configured to detect intracardiac electrograms (IEGMs) and evoked responses from the heart in response to an applied stimulus, thereby aiding in the detection of capture.

For completeness, it is recognized that the IEGM amplifier could also be used to detect the paced depolarization integral (PDI) signal, the T-wave signal for purposes of measuring the QT interval, oxygen saturation, and other physiological signals that may be used to detect pre-ejection interval (e.g., heart sounds, impedance changes, etc.).

For a complete description of PDI, also known as the ventricular depolarization gradient, see U.S. Pat. No. 4,759,366, to Callaghan, which patent is incorporated herein by reference.

For a complete description of QT interval, also known as the stimulus-to-evoked T-wave, see U.S. Pat. No. 4,644,954, to Wittkampf et al., which patent is incorporated herein by reference.

For a complete description of oxygen saturation, see U.S. Pat. No. 4,399,820, to Wirtzfeld et al., which patent is incorporated herein by reference.

And, for a complete description of pre-ejection period and ejection fraction sensors, see U.S. Pat. Nos. 4,865,036 and 5,154,171, both to Chirife, which patents are also incorporated herein by reference.

The dual-chamber pacemaker 10 is controlled by a control system 32 that typically includes a microprocessor to carry out control and timing functions. The control system 32 receives output signals from the atrial amplifier 26, the ventricular amplifier 28, and the IEGM 30 over the signal lines 34, 36 and 38, respectively. These output signals are generated each time a P-wave, R-wave or an evoked response is sensed within the heart.

The control system 32 also generates trigger signals that are sent to the atrial pulse generator 22 and the ventricular pulse generator 24 over the signal lines 40, 42, respectively. These trigger signals are generated each time that a stimulation pulse is to be generated by the respective pulse generators 22, 24. During the time that either an A-pulse or V-pulse is being delivered to the heart, the corresponding amplifier 26, 28 is typically disabled by way of a blanking signal presented to these amplifiers 26, 28 from the control system 32 over the signal lines 44, 46. The blanking action also prevents the amplifiers 26, 28 from becoming saturated from the relatively large stimulation pulses that are present at their input terminals during this time and helps prevent residual electrical signals present in the muscle tissue as a result of the pacer stimulation from being interpreted as P-waves or R-waves.

The pacemaker 10 also includes a memory circuit 48 that is coupled to the control system 32 over a suitable data/address bus 50. This memory circuit 48 allows certain control parameters, used by the control system 32 in controlling the operation of the pacemaker 10 to be programmably stored and modified, as required, in order to customize the pacemaker's operation to suit the needs of a particular patient. Further, the data sensed during the operation of the pacemaker 10 may be stored in the memory circuit 48 for later retrieval and analysis.

A clock circuit 52 directs appropriate clock signals to the control system 32 as well as to any other needed circuits throughout the pacemaker 10 (e.g. to the memory) by the clock bus 54.

The pacemaker 10 also includes a telemetry communications circuit 56. This telemetry circuit 56 is connected to the control system 32 by way of a suitable command/data bus 58. In turn, the telemetry circuit 56, which is included within the implantable pacemaker 10, may be selectively coupled to an external programming device 60 by an appropriate communication link 62, which communication link 62 may be any suitable electromagnetic link. Advantageously, through the external programmer 60 and the communication link 62, desired commands may be sent to the control system 32. Similarly, through this communication link 62 with the programmer 60, data commands (either held within the control system 32, as in a data latch, or stored within the memory 48) may be remotely received from the programmer 60. Similarly, data initially sensed through the leads 12 or 14, and processed by the microprocessor control system 32, or other data measured within or by the pacemaker 10, may be stored and uploaded to the programmer 60.

The pacemaker 10 additionally includes a battery 64 which provides operating power to all of the circuits of the pacemaker 10 via a POWER signal line 66.

The pacemaker 10 includes a first sensor 68 that is connected to the control system 32 of the pacemaker 10 over a suitable connection line 72. The first sensor 68 should be one suitable to detect rest or activity levels such as a piezoelectric crystal, that is mounted to the case of the pacemaker and generates an activity sensor signal, an accelerometer, an activity variance sensor system, or an inclinometer. It is only essential that this activity sensing circuit accurately determine when the patient is at rest so that an accurate baseline measurement can be determined.

The pacemaker 10 also includes a second sensor 70 for purposes of controlling the rate-responsive pacemaker functions. The second sensor 70 is connected to the control system 32 over a suitable connection line 84. The second sensor 70 is preferably a physiologic sensor that requires calibration of the baseline value.

For illustration purposes, in the present embodiment, the second sensor 70 is a minute ventilation sensor, but it is recognized that paced depolarization integral (PDI), QT interval, pre-ejection period (PEP), oxygen saturation, etc. would also benefit from the present invention. The type of sensor used is not critical to the present invention. Such sensors are commonly used with rate-responsive pacemakers in order to adjust the rate (pacing cycle) of the pacemaker 10 in a manner that tracks the physiological or metabolic needs of the patient.

As such, the second sensor 70 comprises a minute ventilation sensor which includes excitation circuitry for generating a constant current pulse (e.g., of about 1 ma and 15 µs) and impedance measuring circuitry for measuring the resulting voltage and calculating the impedance.

The second sensor 70 is shown simplistically connected to the ventricular lead 14 via signal line 76. In practice, the constant current circuitry of the second sensor 70 is coupled to the ring electrode 21 and the voltage measuring circuitry is coupled to the tip electrode 20. In addition, the second sensor 70 utilizes the case electrode as a reference point. The second sensor 70 is then connected to the control system 32 via signal line 84.

In the preferred embodiment, the pacemaker 10 operates in a dual-chamber mode and is electrically connected to the heart of the patient via two leads 12, 14. However, it is well within the scope of this invention to operate this pacemaker 10 in a wide variety of modes including single-chamber or dual-chamber modes, cardioverter or defibrillator modes, unipolar or bipolar modes, etc.

In operation, the second sensor 70 generates an excitation signal between ring electrode 21 and the case electrode and then senses the voltage between the tip electrode 20 and the case electrode. The resultant voltage is then transmitted to control system 32 for determination of the impedance value indicative of the respiration of the patient and for ultimate control of the pacing rate, as is well known in the art. For a more detailed description of this method of monitoring minute ventilation, see, for example, U.S. Pat. No. 5,562,712, issued Oct. 8, 1996 to Steinhaus et al., entitled "Minute Volume Rate-responsive Pacemaker using Dual Unipolar Leads".

To accurately calculate the change in impedance during the exercise state, a baseline impedance must be accurately known.

Figure 2:
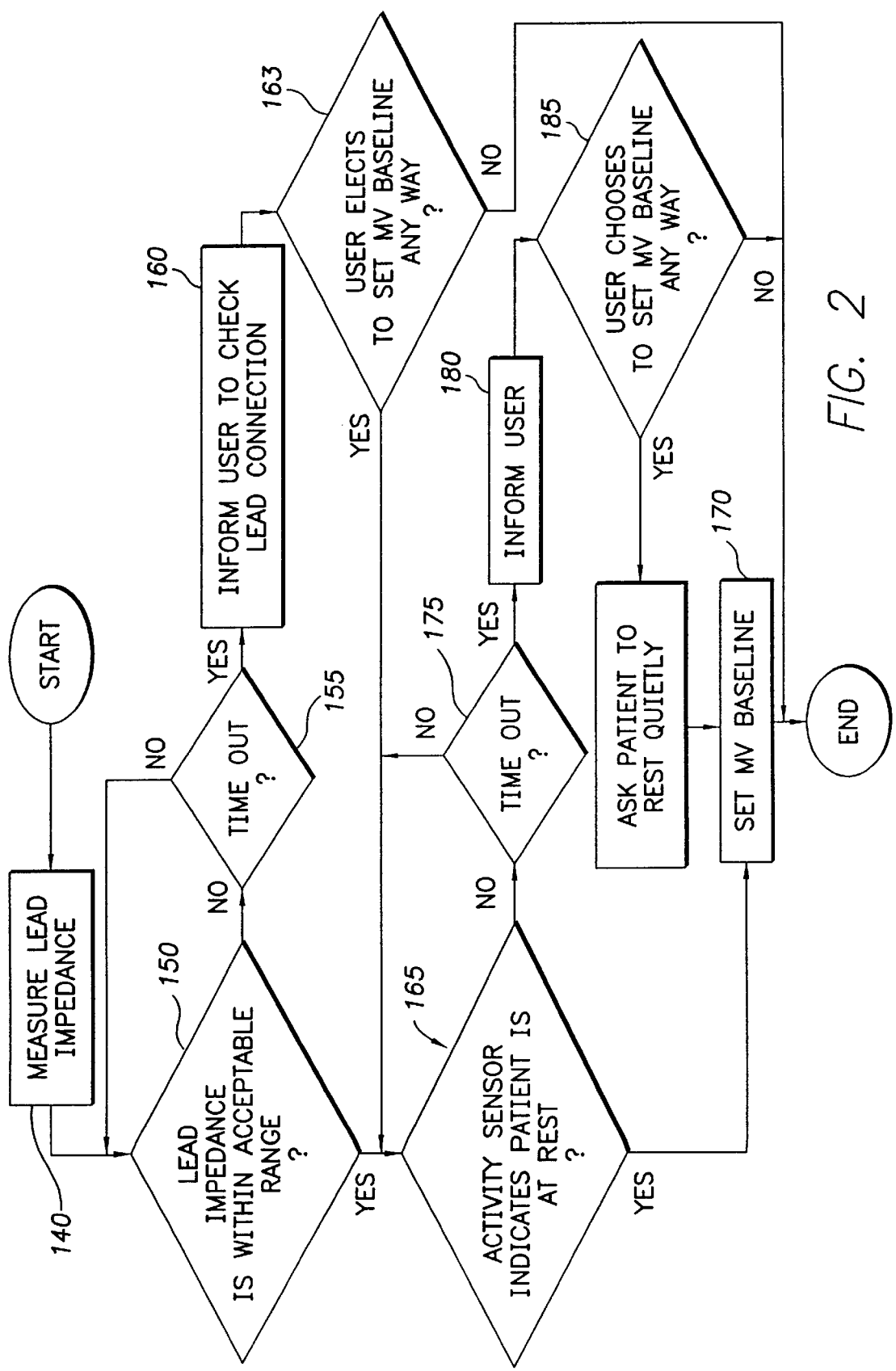
FIG. 2 shows a flow chart for determining the baseline impedance measurement upon implantation in accordance with the present invention.

FIG. 2 sets forth a first method used by the control system 32 to determine the baseline impedance when the clinician is interacting with the system either at implant or at a follow-up visit.

In the preferred embodiment, upon a request to measure the baseline, the control system 32 first triggers a lead impedance measurement (Block 140) to test the proper functioning of the lead. The control system 32 then determines if the lead impedance is within the tolerance range of approximately 300 to 2000 ohms (Block 150).

Lead impedance measurement circuitry is well known in the art and often is shown as a separate circuit coupled to the desired lead. However, in the present embodiment, the second sensor 70 is preferably configured to measure lead impedance, as well as impedances associated with minute ventilation, the only difference being that the pulse generator 24 is typically used as the excitation source during lead impedance measurements.

If the lead impedance is not within the acceptable range, then the control system 32 waits and rechecks the lead impedance until a predetermined time-out is reached (Block 155). After the time-out has expired, the control system 32 notifies the attending clinician via the telemetry circuit 56 to check the lead connections (Block 160). At this point, if the lead connections are correct, the clinician can override the impedance signal and elect to set the baseline at the current level (Block 163).

If the lead impedance is within the acceptable range, the control system 32 next checks the first sensor 68 to determine if the patient is at rest (Block 165). If the first sensor 68 indicates that the patient is at rest, then the baseline impedance is calibrated (Block 170).

If the first sensor 68 indicates that patient is not fully at rest, the control system 32 waits and rechecks the signal until a predetermine time-out is reached (Block 175). If the time-out expires and the first sensor 68 does not indicate that the patient is at rest, the clinician is notified via the telemetry circuit (Block 180).

At this point, the clinician can override the activity sensor signal and elect to set the baseline at the current level (Block 185). The control system 32 then uses the established baseline to determine the baseline metabolic signal, in this case, the minute ventilation baseline signal.

While the flow chart of FIG. 2, indicates that the lead impedance measurement is performed before the activity measurement, it is within the spirit of the invention to reverse that order.

It is also within the spirit of the invention to automatically perform the steps shown in FIG. 2, to recalibrate the second sensor 70 whenever the patient is at rest post-implant.

Figure 3:
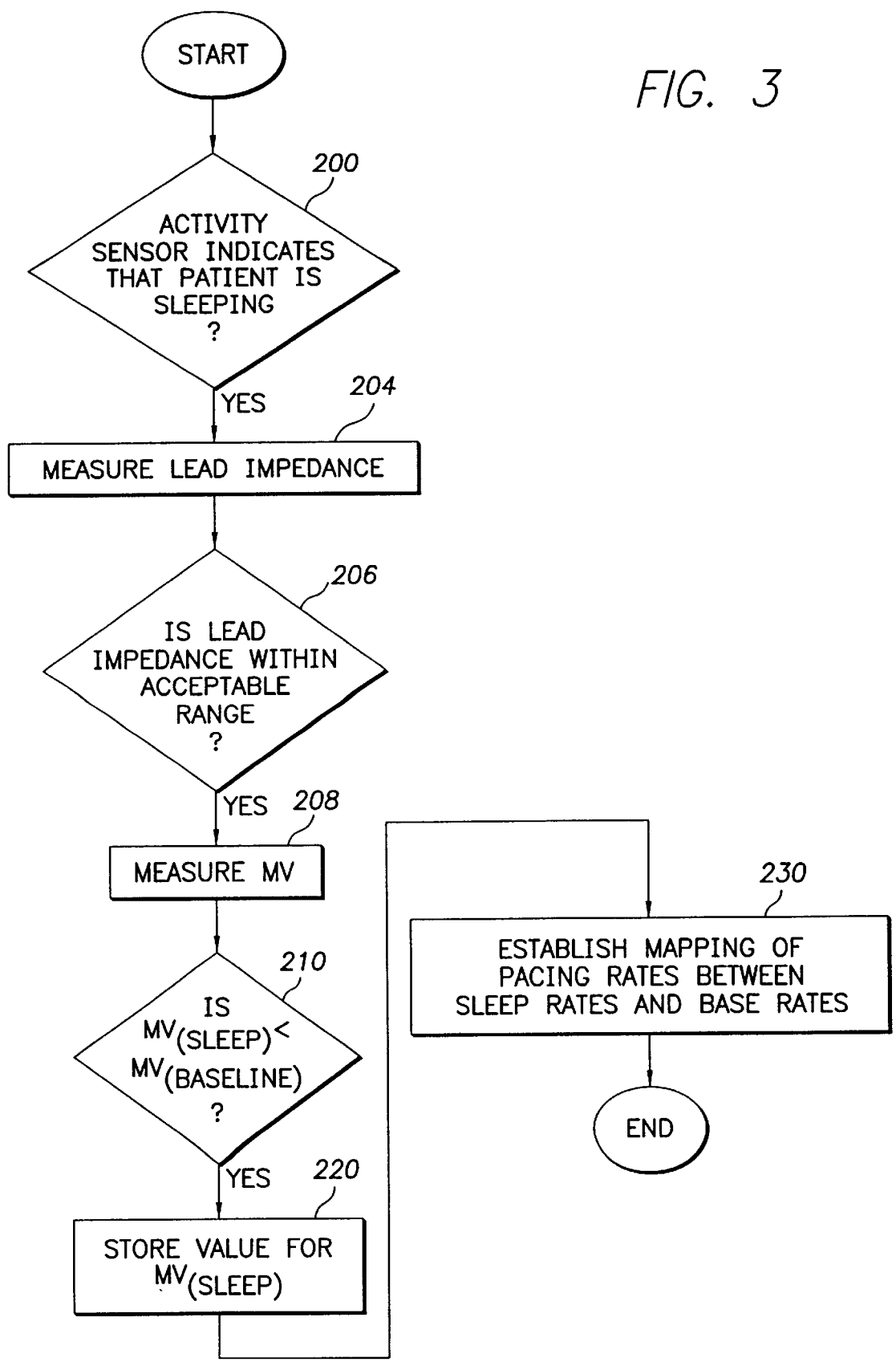
FIG. 3 shows a flow chart for determining an appropriate pacing rate corresponding to the impedance measurement measured during sleep in accordance with the present invention.

FIG. 3 shows another embodiment for automatically and periodically determining the value of the physiological sensor in accordance with the sleep state. In this embodiment, the control system 32 can further detect the sleep state of the patient so that a lower pacing rate may be determined for the patient during sleep.

For a detailed description of how to adapt an activity sensor to determine sleep, see U.S. Pat. No. 5,476,483, to Bornzin et al., entitled "System and Method for Modulating the Base Rate During Sleep for a Rate-responsive Cardiac Pacemaker", which patent is incorporated herein by reference. Briefly, Bornzin et al. teaches the use of activity variance to determine if the patient is at rest or sleeping. That is, an activity sensor has significantly less variability during sleep.

Once the first sensor 68 indicates that the patient is sleeping (Block 200), the control system 32 then triggers a lead impedance measurement (Block 204) to test the proper functioning of the lead. The control system 32 then determines if the lead impedance is within the tolerance range of approximately 300 to 2000 ohms (Block 206).

The control system 32 next measures a current MV value (Block 208) to determine if the MV value during sleep, MV (sleep), is less than the baseline MV value, MV (baseline). If the delta MV=MV (baseline), MV (sleep) value is a negative value (i.e., indicating that the current value is smaller that the previous baseline value, then the control system 32 stores the value of the MV (sleep), either as a single point measurement, or as an average of the lowest values, etc. (Block 220).

In the preferred embodiment, as shown in FIG. 3, the control system 32 then associates the new MV (sleep) value with the sleep rate and establishes a map of pacing rates between a sleep rate and the base rate using (Block 230), for example, a predetermined transfer curve.

This cycle of testing the delta MV value during sleep may be performed once during sleep, or may be performed throughout the sleep state to determine the lowest value.

From the above description, it can be seen that the control system 32 calibrates both a resting value and a sleep value, based on a first sensor 68 that can detect both states.

Alternately, it is possible to automatically calibrate a baseline for the second sensor 70 when the patient is sleeping and to provide appropriate mapping of values for the "alert-resting" state (e.g., sitting, resting in a reclining state, but not yet sleeping, etc.).

Although the invention has been described with reference to particular embodiments, it is to be understood that these embodiments are merely illustrative of the application of the principles of the invention. For instance, this method of determining and maintaining the calibration can be used in association with any monitored physiologic parameter (e.g., contractility, blood oxygen, respiration, etc.) that depends upon the lead integrity and a baseline value determined at rest. Accordingly, the embodiments described in particular should be considered exemplary, not limiting, with respect to the following claims.

What is claimed is:

1. An implantable rate-responsive cardiac stimulation device for stimulating a patient's heart, the device being adapted to connect to at least one implantable lead, comprising:

a pulse generator, coupled to the at least one implantable lead, that generates stimulation pulses;

a physiologic sensing circuit, coupled to the at least one implantable lead, that senses a physiological signal for generating a signal indicative of metabolic demand;

a control circuit, coupled to the pulse generator and the physiologic sensing circuit, that triggers the pulse generator to deliver stimulation pulses in response to the metabolic demand signal.

2. The implantable cardiac stimulation device, as set forth in claim 1 wherein:

the activity sensing circuit can discriminate between resting and sleeping states; and wherein the reduced activity state signal indicates that the patient is resting.

3. The implantable cardiac stimulation device, as set forth in claim 1 wherein:

the activity sensing circuit can discriminate between resting and sleeping states; and wherein the reduced activity state signal indicates that the patient is sleeping.

4. The implantable cardiac stimulation device, as set forth in claim 1 wherein the physiologic sensing circuit is an impedance measuring circuit, coupled to the at least one implantable lead and wherein the control circuit measures the lead impedance during the reduced activity state so as to verify lead contact with cardiac tissue.

5. The implantable cardiac stimulation device, as set forth in claim 4, wherein:

the at least one predetermined criteria is the lead impedance having a value being between 300 and 2000 ohms to verify tissue contact.

6. The implantable cardiac stimulation device, as set forth in claim 1, wherein:

the physiologic sensing circuit comprises minute ventilation measuring circuitry coupled to the lead; and the physiologic signal represents minute ventilation.

7. The implantable cardiac stimulation device, as set forth in claim 1, wherein:

the physiologic sensing circuit comprises circuitry that integrates an evoked R-wave signal; and the physiologic signal represents paced depolarization integral (PDI).

8. The implantable cardiac stimulation device, as set forth in claim 1, wherein:

the physiologic sensing circuit comprises circuitry that detects a T-wave following an evoked R-wave and measures the time therebetween; and the physiologic signal represents QT interval.

9. The implantable cardiac stimulation device, as set forth in claim 1, wherein:

the physiologic sensing circuit comprises circuitry that detects one of a pre-ejection interval or ejection interval; and the physiologic signal corresponds to a contractility signal.

10. An implantable rate-responsive cardiac stimulation device for stimulating a patient's heart, the device being adapted to connect to at least one implantable lead, comprising:

pulse generating means for generating stimulation pulses;

physiologic sensing means for sensing a physiological signal indicative of metabolic demand;

activity sensing means for generating an activity state signal indicating when the patient is active or at rest; and processing means, responsive to the physiologic sensing means, for triggering the pulse generating means to deliver stimulation pulses at a rate in accordance with the physiological signal, and for calibrating the physiologic sensing means based on the physiologic signal when the activity state signal Indicates that the patient is at rest.

11. The implantable cardiac stimulation device, as set forth in claim 10, wherein:

the activity sensing means includes means for discriminating between alert-resting and sleeping; and the activity state signal further includes a sleep signal indicating the patient is sleeping.

12. The implantable cardiac stimulation device, as set forth in claim 10 wherein the physiologic sensing means comprises:

impedance measuring means, coupled to the at least one implantable lead and the processing means, for measuring a lead impedance during the stimulation pulse so as to verify lead contact with cardiac tissue.

13. The implantable cardiac stimulation device, as set forth in claim 12, wherein:

the lead impedance must have a value being between 300 and 2000 ohms to verify tissue contact.

14. In an implantable rate-responsive cardiac stimulation device having a pulse generator adapted to deliver stimulation pulses via an implantable lead to a patient's heart, a method comprising the steps of:

generating stimulation pulses;

sensing a physiologic signal indicative of metabolic demand;

sensing when the patient is in a resting state;

triggering the pulse generator to deliver stimulation pulses at a rate in accordance with the physiologic signal, and calibrating the sensing of the physiologic signal when the patient is at rest.

15. The method, as set forth in claim 14, wherein:

the step of sensing when the patient is in a resting state further includes the step of discriminating between alert-resting and sleeping; and the step of calibrating the sensing of the physiologic signal further includes calibrating the physiologic signal whenever the patient is sleeping.

16. The method, as set forth in claim 14, further comprising:

measuring a lead impedance during a stimulation pulse so as to verify lead contact with cardiac tissue; and wherein the step of calibrating the sensing of the physiologic signal further includes calibrating the physiologic signal when the lead impedance is within a normal range and the patient is resting.

* * * * *

UNITED STATES PATENT AND TRADEMARK OFFICE
CERTIFICATE OF CORRECTION

PATENT NO.   : 6,188,927 B1
DATED        : February 13, 2001
INVENTOR(S)  : Richard Lu and David W. Adinolfi It is certified that error appears in the above-identified patent and that said Letters Patent is hereby corrected as shown below:

Column 8,
Line 20, delete "." insert
 -- ;
    an activity state sensing circuit configured to detect when the patient is in
a reduced activity state; and wherein
    the control circuit is configured to determine a baseline metabolic
demand signal value at the detected reduced activity state to thereby adapt the
delivery of stimulation pulses according to the metabolic demand signal and the
baseline metabolic demand signal value. --

Signed and Sealed this

Eighth Day of February, 2005

JON W. DUDAS
*Director of the United States Patent and Trademark Office*